United States Patent [19]

Wirtzfeld et al.

[11] 4,399,820
[45] Aug. 23, 1983

[54] PROCESS AND DEVICE FOR REGULATING THE STIMULATION FREQUENCY OF HEART PACEMAKERS

[76] Inventors: Alexander Wirtzfeld, No. 26 b, Haupstrasse, 8191 Thanning; Roland Heinze, No. 13, Wilhelm Diess Weg, 8000 München 81; Thomas Bock, No. 48, Türkenbundweg, 8000 München 21; Hans D. Liess, No. 106, Fasanenstrasse, 8025 Unterhaching, all of Fed. Rep. of Germany

[21] Appl. No.: 346,315

[22] Filed: Feb. 5, 1982

[30] Foreign Application Priority Data

Feb. 26, 1981 [DE] Fed. Rep. of Germany ...... 3107128

[51] Int. Cl.³ ............................................. A61N 1/36
[52] U.S. Cl. ............................................. 128/419 PG
[58] Field of Search ............... 128/632, 633, 637, 668, 128/695, 419 PG

[56] References Cited

U.S. PATENT DOCUMENTS 4,202,339 5/1980 Wirtzfeld et al. ............ 128/419 PG

FOREIGN PATENT DOCUMENTS 2741981 4/1978 Fed. Rep. of Germany ...... 128/633

OTHER PUBLICATIONS

"A New Instrument for the Simultaneous Measurement of Total Hb . . . " Leslie J. Brown, IEEE Trans on Biomed. Engineering, vol. BME27, No. 3, Mar. 1980.
"A New Pacemaker Autoregulating the Rate of Pacing in Relation to Metabolic Needs" Camilli et al. Conference-Proc. of the 5th Int. Symp. on Cardiac Pacing, Tokyo, Japan, Mar. 14-18, 1976.
The Principle, Design and Features of a New Hb-Oximeter, F. J. Janssen, Medicamundi, vol. 17, No. 1, (1972).
A New Instrument for Rapid Measurement of Blood Oxygen Saturation and Hb Concentration Bio Med Eng. (GB), vol. 5, No. 11, (Nov. 1970).

Primary Examiner—William E. Kamm
Assistant Examiner—Mitchell J. Shein
Attorney, Agent, or Firm—John C. Smith, Jr.

[57] ABSTRACT

A process and a device for regulating the stimulation frequency of heart pacemakers are disclosed. The process comprises generating with the aid of light emitted by a light-emitting element, reflected by the blood of a patient, and received by a light-receiving element, a current flow which causes, in a measuring probe, an increasing of the current flow at a constant probe voltage or a damping of the probe voltage at constant current flow. Thereafter, one of the possible changing values is measured and the change, with time, is evaluated as a measured quantity proportional to the change, with time, of the blood oxygen saturation, and, as a function of the measured quantity, the stimulation frequency of the heart pacemaker is regulated in such a manner that the greatest possible blood oxygen saturation is always achieved with the lowest stimulation frequency. The device for practicing the invention comprises a measuring probe containing at least one combination of only two active optoelectronic elements, one light-emitting element and one light-receiving element; a control circuit electrically connected to the measuring probe; a stimulation catheter in which the measuring probe is incorporated, and at least two electric lines leading through the stimulation catheter and electrically connecting the measuring probe to the control circuit of the measuring probe.

18 Claims, 11 Drawing Figures

PROCESS AND DEVICE FOR REGULATING THE STIMULATION FREQUENCY OF HEART PACEMAKERS

BACKGROUND OF THE INVENTION

This invention relates to a process and a device for regulating the stimulation frequency of heart pacemakers. The device can thus be used in all patients requiring a heart pacemaker.

The invention has the aim, in heart pacemaker patients, of optimally covering the oxygen demand of the body via the blood circulation, so that the pulse frequency of the heart, as in the natural case, adapts to the particular load conditions, the optimum hemodynamic situation being found by the pacemaker itself.

In spite of the extended pacemaker function, the invention has, at the same time, the aim of virtually not changing the hitherto well-proved embodiment of the heart pacemakers and the associated pacemaker catheters, so that the known implantation techniques remain the same and, also, the high requirements with respect to the long-term use can be fulfilled.

In the case of heart pacemakers, controlling the pacemaker frequency via a measurement of the central venous oxygen saturation and thus adapting the frequency to the particular load conditions has already been described in DE-OS (German Offenlegungsschrift) No. 27 17 659. In this known process, the measurement of the blood oxygen saturation is carried out with the aid of a light-guide probe which is incorporated in the stimulation catheter. The measurement principle of reflection oximetry, which is used in the process, is based on the determination of the reflection intensities of light of the measured wavelength of 660 nm (R660) and of the reference wavelength of approximately 800 nm (R800) in the blood. A characteristic of the applied frequency adaptation is a firm association of the pacemaker frequency f with each determined measured value of the oxygen saturation $S_{O2}$ $$f = k \cdot S_{O2}, \text{ wherein } f_{min} < f < f_{max}.$$

The values for k, $f_{min}$ and $f_{max}$ must be fixed before the implantation.

Furthermore, it is known from DE-OS (German Offenlegungsschrift) No. 21 13 247 that the ratio of the two measured values $R_{800}/R_{660}$ is directly proportional to the blood oxygen saturation $S_{O2}$ expressed by the ratio $HbO2/(HbO2 + Hb)$ (wherein Hb represents hemoglobin and HbO2 represents oxyhemoglobin).

The heart pacemakers constructed according to the principle indicated in DE-OS (German Offenlegungsschrift) No. 27 17 659 exhibit a number of problems which have hitherto hindered a clinical use of pacemakers of this kind:

The measurement method does not tolerate any changes in the optical transmission path (light guide, reflection space and coupling points), which cause a wavelength-dependent effect on the signal. This can occur through defective coupling points; material changes in the light guide; deposits on the light opening in the catheter, and foreign objects in the reflection region (heart wall, trabeculae).

Furthermore, the control of the pacemaker frequency in dependence on the oxygen saturation, according to a fixed prescribed characteristic curve, can have disadvantageous consequences if, on advancement of the basic cardiac illness, a change in the relationship of power of the heart to pulse frequency occurs. A deterioration in the hemodynamics can even occur through too great an increase in the frequency.

The measurement principle and control principle require a calibration before the implantation and correspondingly increase the service requirements.

In addition, the catheter has only a limited serviceability, since the end supports of the light guides become unstable over long periods because they have to accept the greatest part of the tensile strain acting on the catheter.

In addition, the fatigue strength of the light guides for long-term use is not given with the materials available at present, and the necessity of arranging the light aperture laterally in the combination catheter allows no margin technically for the further introduction of a mandrin (steel wire which is pushed into the highly elastic catheter during the implantation, in order more easily to introduce the catheter into the ventricle) beyond this point. In addition, the coupling system between the combination catheter and the pacemaker is much more complicated in the production, sensitive in use and voluminous than in the case of conventional pacemaker technology.

Since the energy losses while using the light-guide technique and the measuring principle mentioned can only be kept small by means of high optical precision, the costs for the total system compared with conventional technology increase several-fold.

SUMMARY OF THE INVENTION

It is an object of this invention to avoid the disadvantages described above and to provide a measuring process and a device for the determination of the blood oxygen saturation. Another object of the invention is to provide a process and a device for regulating the stimulation frequency of heart pacemakers so that a long-term, undisturbed data acquisition and the best possible hemodynamic situation in the blood circulation are guaranteed, and at the same time the operational safety is not decreased but increased as much as possible, it being intended to employ non-critical servicing and production practices which have been proved technically over long periods of time.

To attain these objects the present invention provides a process for regulating the stimulation frequency of heart pacemakers which comprises the steps of generating with the aid of light emitted by a light-emitting element and reflected by the blood of a patient, in a light-receiving element, a current flow which causes, in a measuring probe, an increasing of the current flow at a constant probe voltage or a damping of the probe voltage at constant current flow; measuring one of the possible changing values; evaluating the change, with time, as a measured quantity proportional to the change, with time, of the blood oxygen saturation, and regulating, as a function of the measured quantity, the stimulation frequency f of the heart pacemaker in such a manner that the greatest possible blood oxygen saturation is always achieved with the lowest stimulation frequency.

For carrying out this process, the present invention provides a device for the frequency regulation of heart pacemakers having a stimulation frequency which adapts itself to the load conditions of a patient, the central venous blood oxygen saturation being opto-electronically measured as a reference or control quantity for the adaptation, this measurement being carried out with the aid of an intracardiac measuring probe, and the acquisition and evaluation of the measured value occurring by means of a circuit additionally arranged in the heart pacemaker, said device comprising a measuring probe containing at least one combination of a single active light-emitting element and a single active light-receiving element; a control circuit electrically connected to the measuring probe; a stimulation catheter in which the measuring probe is incorporated, and at least two electric lines leading through the stimulation catheter and electrically connecting the measuring probe to the selection circuit of the measuring probe.

The advantages which are achieved with the invention are as follows:

The catheter with the measuring probe according to the invention is virtually identical in its mechanical construction with the bipolar catheters which have long been in use, and accordingly entails no additional problems with respect to the long-term mechanical strength and the implantation technique and has the best properties with respect to a long-term optical measurement of the blood oxygen saturation.

The data acquisition makes it possible to manage with only two electric lines (wire windings) in the catheter, and thus to use the well-proved catheter techniques.

The data processing makes it possible to measure, with uniform accuracy, normal variations with time in the body load of the patient, independently of very short or long-term changes along the measuring distance.

The regulating process for adapting the stimulation frequency to the loads of the patient makes possible a direct re-adjustment in the case of variations in the load as well as an autonomous optimum regulation in the context of a best possible oxygen supply with as small a heart load as possible, thus as low a stimulation frequency as possible.

The detection of errors makes possible the recognition of failures in the data acquisition and evaluation and due to breaks in the electric lines in the catheter, and makes possible the known use of two lines for the vital stimulation.

BRIEF DESCRIPTION OF THE DRAWINGS

Two embodiments of the invention will now be described by way of example and with reference to the accompanying drawings in which.

DESCRIPTION OF THE PREFERRED EMBODIMENTS

Figure 1:
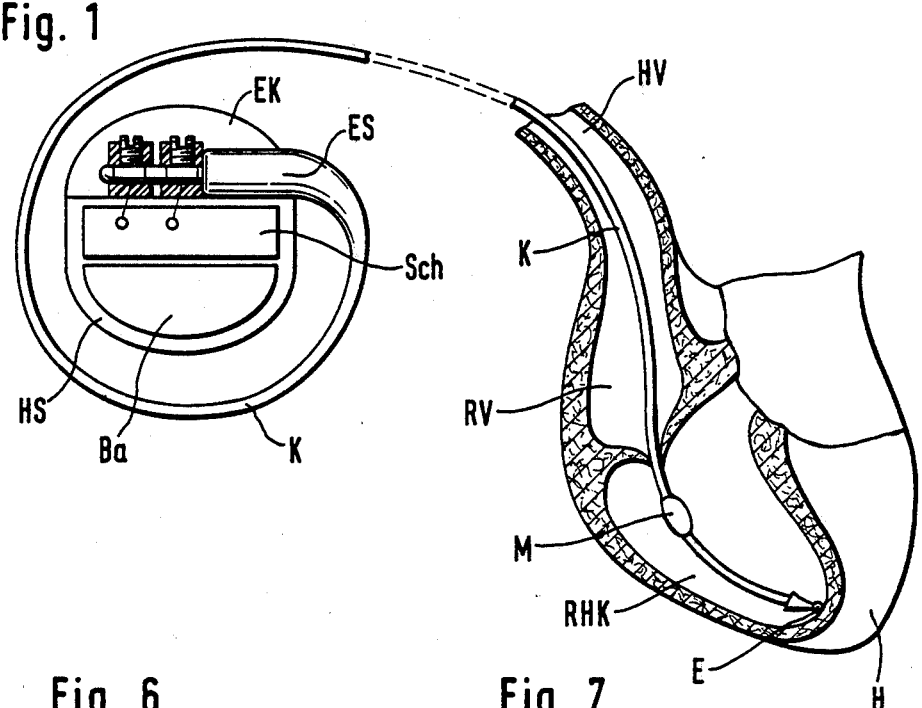
FIG. 1 is a diagrammatic view showing a heart pacemaker with a stimulation catheter and measuring probe for stimulation of a heart muscle.

FIG. 1 shows a heart pacemaker HS containing a power supply component Ba, an electronic circuit component Sch and a bipolar electrical connector EK. A bipolar electrical plug ES of a stimulation catheter K is firmly screwed into the electrical connector EK. The stimulation catheter K leads via the superior vena cava HV into the right auricle RV and then into the right ventricle RHK of a patient, so that, at this point, the blood oxygen saturation is measured by a measuring probe M and the heart muscle H is stimulated by a stimulation electrode E.

Figure 2:
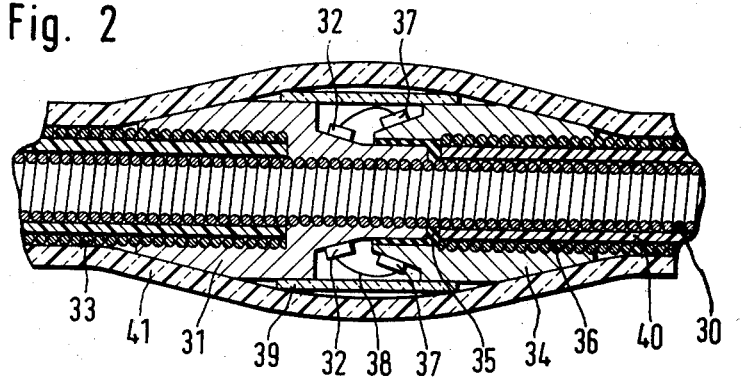
FIG. 2 is a longitudinal section, on an enlarged scale, through the measuring probe provided by concentrically arranged electric lines in the form or wire windings.
Figure 3:
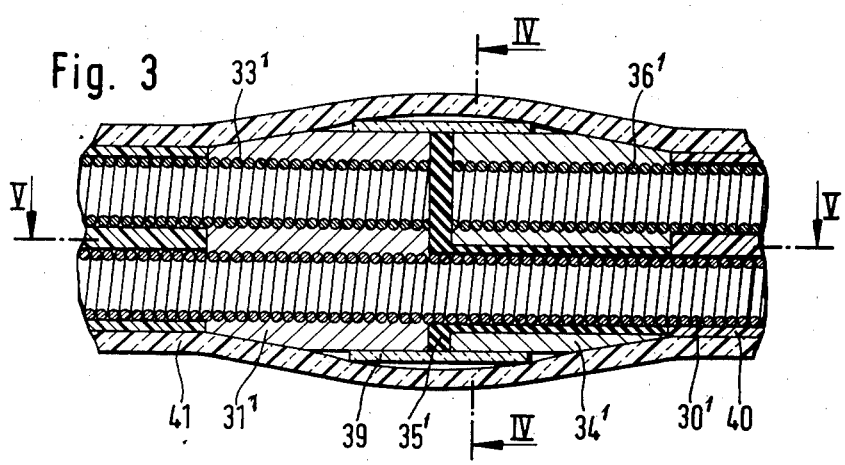
FIG. 3 is a longitudinal section through a further embodiment of a measuring probe with electric lines in the form of wire windings arranged in parallel.
Figure 4:
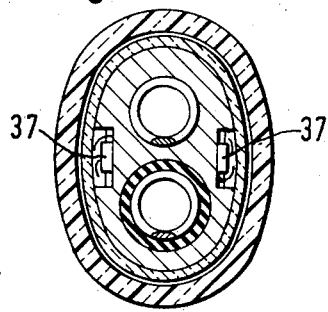
FIG. 4 is a section along line IV—IV of FIG. 3.
Figure 5:
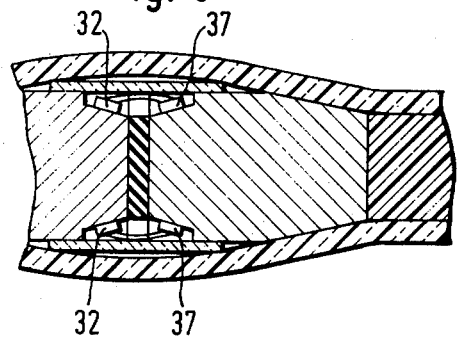
FIG. 5 is a section along line V—V of FIG. 3.

Two embodiments of a measuring probe are shown in more detail in FIG. 2 and in FIGS. 3 to 5, respectively. There are essentially two forms of construction of the bipolar stimulation catheters in use at the present time. In both forms of construction, the two electric lines are wire windings 30 and 36. The wire windings 30 and 36 are arranged concentrically with one another in the embodiment shown in FIG. 2, whereas in the embodiment shown in FIGS. 3, 4 and 5 wire windings $30^1$ and $36^1$ are used which extend parallel to each other.

In the embodiment as a combined measuring catheter and stimulation catheter, both wire windings 30 or $30^1$ and 36 or $36^1$ serve as a supply line to the stimulation electrode E and also as the current supply to the measuring probe M. The electrical contact with the measuring probe M occurs via a first metallic annular element 31 in FIG. 2 and a first metallic annular element $31^1$ in FIG. 3. This first annular element has an inner thread which ensures a permanent pressure contact, and simultaneously serves as a carrier for at least one light-transmitting element 32 which is a red-light-emitting diode in each case and which is in contact, e.g. in adhesive contact, at the cathode side, with the first metallic annular element. Furthermore, the first metallic annular element is electrically connected, via threaded and/or pressure contact, with a wire winding 33 in FIG. 2 and $33^1$ in FIG. 3 each of which also leads to the stimulation electrode E and is provided as a spare component, as a safety device for the stimulation. An annular insulation 35 in FIG. 2 and $35^1$ in FIG. 3 which is firmly adhesively bonded is mounted between the plug-side part of the first metallic annular element and a second annular metallic element 34 in FIG. 2 and $34^1$ in FIG. 3. The second annular metallic element has threaded and/or pressure contact with the probe line, i.e. with the wire winding 36 in FIG. 2 and $36^1$ in FIG. 3, and serves as a carrier for one or more light-receiving elements 37 which may be a phototransistor in each case. If a bridging diode $D_o$, not shown in FIGS. 2 and 3, is not integrated in the light-receiving element or the light-emitting element it must be additionally attached, as an individual element, to one of the two annular elements 31 or 34 in FIG. 2 or $31^1$ or $34^1$ in FIG. 3. The second supply line to the light-emitting and light-receiving elements 32 and 37 (or to the bridging diode) is, in each case, a bond wire 38 from the opposite annular element.

As a protection for the light-emitting and light-receiving elements, a transparent protective jacket 39, preferably a glass ring, surrounds the body of the measuring probe composed of the two annular metallic elements, the glass ring 39 being firmly welded at its edges to the metallic annular elements which are mutually insulated.

An electrically insulating tube 40 serves as an insulation between the supply lines, i.e. the wire windings, and, on the other hand, an outer transparent insulating tube 41 serves as an insulation from the exterior.

Figures 6, 7:
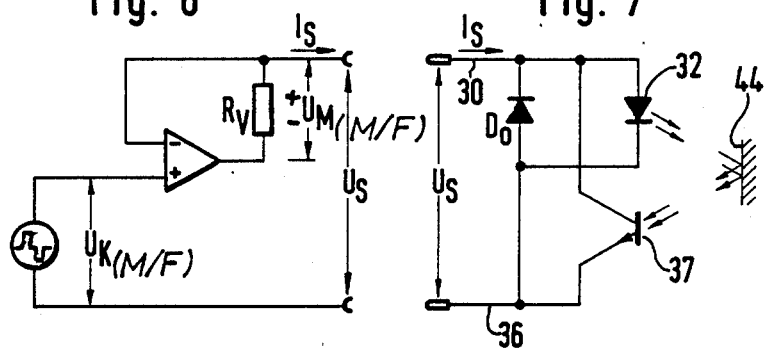
FIG. 6 is a schematic diagram of a control circuit of the measuring probe.
FIG. 7 is a circuit of the measuring probe.

FIG. 7 shows the circuit of the measuring probe M consisting of the light-emitting element 32 in the form of a light diode, the light receiving element 37 in the form of a npn-photo transistor, and the bridging diode $D_o$.

Figure 8:
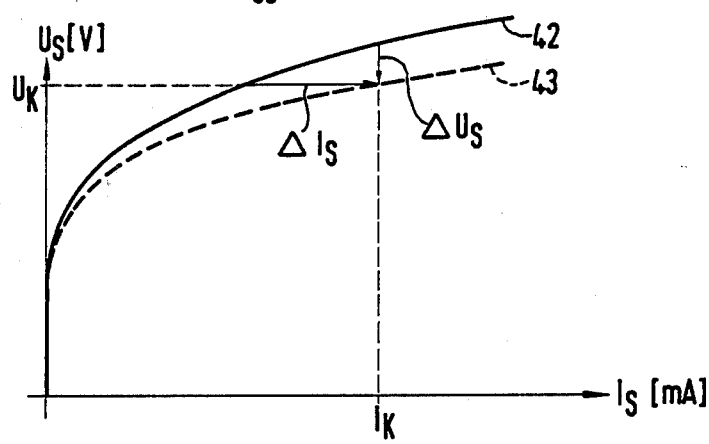
FIG. 8 is a diagrammatic view showing the current-voltage characteristics of the measuring probe.

In FIG. 8, the functional principle of the measuring probe M can be recognized with reference to its current-voltage characteristics 42 and 43. If a reflecting object 44 is lacking in the measuring arrangement of FIG. 7, the I-U characteristic 42 results. However, if light from a reflecting object 44 (in the present case, blood) strikes the light-receiving element 37, the I-U characteristic 43 results.

At constant current $I_K$, the intensity of the reflected light is thus proportional to the change in the voltage $\Delta U_S$, and correspondingly, at constant voltage $U_K$, proportional to the current change $\Delta I_S$.

The above-mentioned combination of light-emitting element and light-receiving element retains the principle of its mode of function, even when connected in parallel with one or two further combinations.

FIG. 6 shows by way of example an embodiment of a control circuit of the measuring probe, which circuit produces a pulse with a constant voltage characteristic at the supply lines, i.e. at the wire windings, to the measuring probe, so that the characteristic (response) curve of the current $I_S$ through the measuring probe is dependent on the reflected light accepted by the measuring probe and thus also the voltage characteristic at a load resistance $R_v$. Thus, if the probe voltage $U_S$ reaches a fixed value $U_K$, the measured voltage $U_M$ at this moment is:

$$U_M = I_S \cdot R_v$$

and thus proportional to the intensity of the light reflected by the blood and accepted by the measuring probe, the reflection factor of the blood, according to the wavelength, being a function of the blood oxygen saturation.

Figure 9:
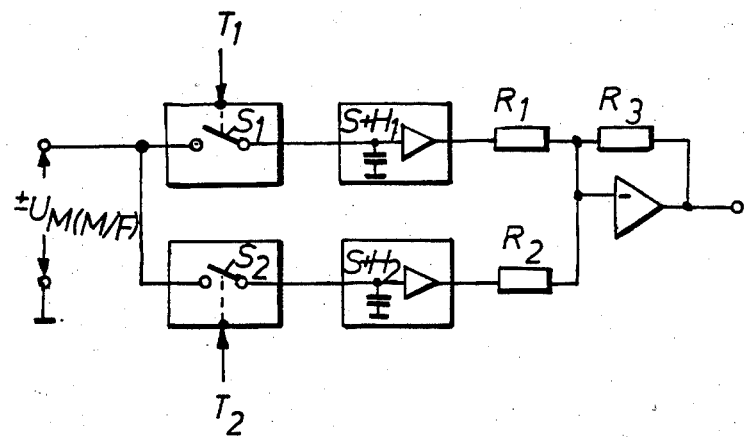
FIG. 9 is a schematic diagram of a signal converter circuit.

FIG. 9 shows the functional principle for an analog circuitry of the signal converter 8. The measured signal $U_M$, consisting of a positive measured pulse $U_{MM}$ arriving in the pulse phase $T_1$ and a negative error-detection pulse $-U_{MF}$ arriving in the pulse phase $T_2$, is thus received by two sample and hold circuits $S+H_1$ and $S+H_2$ so that the storage $S+H_1$ stores the amplitude of the measured pulse $U_{MM}$ via a switch $S_1$ closed in the pulse phase $T_1$ and the other storage $S+H_2$ stores the amplitude of the error-detection pulse $-U_{MF}$ via a switch $S_2$ closed in the pulse phase $T_2$. In the following summation circuitry the signal values $U_M$ and $U_{MF}$ are evaluated in such a manner that the measuring error included in the measured pulse and caused by changes in the resistance of the wire windings 30, 30[1] and 36, 36[1] and a temperature drift of the optical measuring probe M is eliminated.

Figure 10:
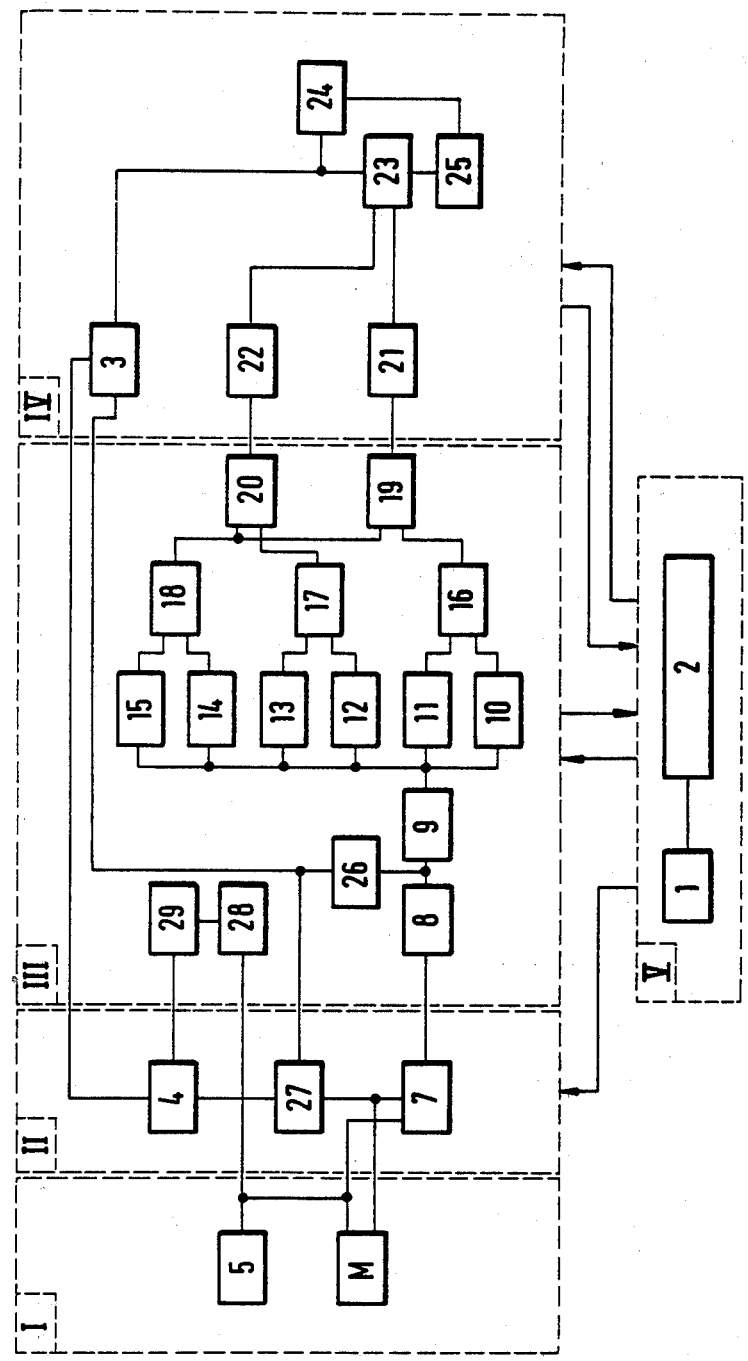
FIG. 10 is a block diagram of a heart pacemaker.

The most important functions of the heart pacemaker according to the invention are represented in FIG. 10. In this figure, the areas enclosed by broken lines indicate the major functional units and denote, in particular:

(I) Catheter;
(II) Catheter control;
(III) Evaluation of measured values;
(IV) Frequency regulation;
(V) Program control.

According to FIG. 10, a fixed-frequency pulse generator 1 gives the time base for a program control 2 which controls all the measuring and regulating processes of the pacemaker circuit.

Depending on a time code prescribed by a stimulation frequency generator 3, the program control 2 starts the transmission of the stimulation pulse by a stimulation pulse generator 4 via a stimulation electrode 5, and directly subsequently the measurement of the blood oxygen saturation via the measuring probe M with a measuring probe control circuit 7. The measured signal is evaluated and amplified in a signal converter 8 and, in the case of using digital data processing, is converted into digital form. An integrator 9 forms the average value of the measured signals over a prescribed period of time. Storages 10 to 15 accept the integrated signal value, the storages 10 and 11 alternately in time period $\Delta t_1$ and the storages 12 and 13 alternately in time period $\Delta t_4$. The highest measured signal value occurring in a prescribed time range $\Delta t_0$ is stored in the maximum value storage 14, and the lowest value in each case is stored in the minimum value storage 15.

In a difference-former 16, the difference $\Delta S_{O2}$ in the measured value between the new and each of the previous measured signals in storage 10 or storage 11 is determined and in a difference-former 17 the difference in the measured value between the contents of storage 12 or 13 is determined. In a difference-former 18, the maximum measured value variation range is $S_{O2max} - S_{O2min} = \Delta S_{O2max}$, so that the ratio, determined in dividers 19 and 20, of short-term measured value variation to maximum variation range yields a normalized measured quantity $B_S$ in each case:

$$B_{S1(4)} = \frac{\Delta S_{O2} \cdot \Delta t_0}{\Delta S_{O2max} \cdot \Delta t_{1(4)}}$$

In the frequency regulation IV, a comparator 21 determines whether the change in the normalized measured quantity $\Delta B_{S1}$ with time is larger or smaller than a predetermined value $+A_1$ or $-A_1$.

In a stimulating frequency control 23 which follows, a change is effected in the stimulating frequency by a positive value $+\Delta f$ in the case in which $\Delta B_{S1} < -A_1$ and by a negative value $-\Delta f$ in the case in which $\Delta B_{S1} > +A_1$, and the sign of the change is stored in a storage 24. In the case in which $-A_1 < \Delta B_{S1} < +A_1$, a change in the stimulation frequency is automatically initiated in the frequency control 23, after a fixed predetermined time interval $\Delta t_5$, the sign of the change being opposite to that which is retained in the storage 24, as long as the tendency control 25 does not effect a repetition of the sign. After the prescribed time interval $\Delta t_4$, a comparator 22 assesses whether the change in the measured quantity $\Delta B_{S4}$ is larger than a fixed value $A_2$ or smaller than $-A_2$, whereupon the preceding frequency change is either reversed or remains.

An error detection 26 compares the signal received by the data evaluation with allowed limiting values and sets the stimulation frequency generator 3 to a fixed frequency $f_0$ if these limiting values are exceeded, and short-circuits, via a switch 27, the two catheter connections, whereby the measurement and regulation are put out of action.

In an electrocardiogram amplifier 28, the intrinsic activity of the heart is monitored between the stimulations, and, in the case of a self-excitation of the heart, the stimulation by the pulse generator is hindered via a comparator 29.

Figure 11:
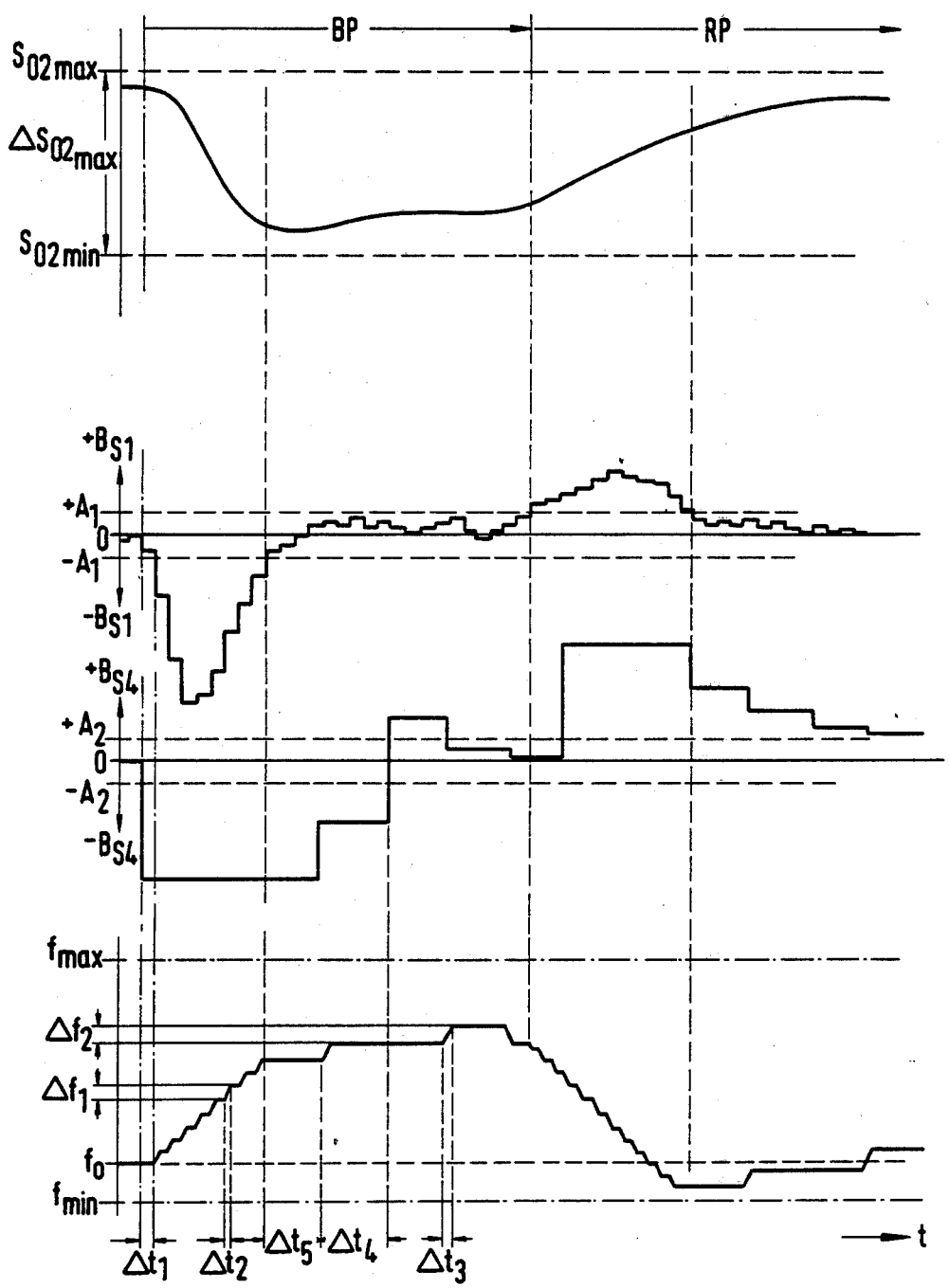
FIG. 11 is a schematic diagram of the variation of the stimulation frequency with time, as a function of the central venous blood oxygen saturation.

FIG. 11 shows the regulation, according to the invention, of the heart pacemaker stimulation frequency f as a function of the load of the patient, represented by the relationship in the variation, with time, of the measured value of the blood oxygen saturation $S_{02}$, the changes therein per time unit $\Delta t_1$ and $\Delta t_4$, and the change in the frequency f effected thereby.

At the beginning of a load phase BP, the central venous oxygen saturation $S_{02}$ decreases, that is to say, the change per time unit $\Delta t_1$, relative to a maximum variation range $\Delta S_{02max}/\Delta t_0$ between the limiting values $S_{02max}$ and $S_{02min}$, gives a negative value for $B_{S1}$. If this is smaller than $-A_1$, a frequency change by $+\Delta f_1$ follows automatically during the course of the time interval $\Delta t_2$. If, in contrast, the oxygen saturation $S_{02}$ reaches, in the load phase BP, a certain equilibrium state, so that the value of $B_{S1}$ oscillates between $-A_1$ and $+A_1$, the optimum regulation begins, in particular always with a positive frequency change $+\Delta f_2$ after $\Delta t_5$, at first, to provide a better supply of oxygen. If this $+\Delta f_2$ causes an increase in the $S_{02}$ value during the course of the time unit $\Delta t_4$, and if this value—again relative to $\Delta S_{02max}/\Delta t_4$ is greater than a fixed value $+A_2$, the frequency change is retained and initiated at the same time, owing to the positive result, a further increase of frequency by $\Delta f_2$ after further $\Delta t_5$. If this does not yield a positive $S_{02}$ change, thus, if the $B_{S4}$ value, after $\Delta t_4$, is smaller than $+A_2$, the frequency change is reversed. If the rest phase RP then begins, and the $B_{S1}$ value increases above the fixed value $+A_1$, a negative frequency change follows automatically until $B_{S1}$ is again smaller than $+A_1$. The optimum regulation then begins again with a positive frequency change $+\Delta f_2$ after $\Delta t_5$, and repeats this until, after $\Delta t_4$, the $B_{S4}$ value is greater than $+A_2$, that is to say, an improvement in the oxygen saturation $S_{02}$ is effected.

The invention may be embodied in other specific forms without departing from the spirit or essential characteristics thereof. The embodiments are therefore to be considered in all respects as illustrative and not restrictive.

What is claimed is:

1. A process for regulating the stimulation frequency of heart pacemakers as a function of the measured change of a physiological parameter of the blood circulation, preferably the central venous oxygen saturation, comprising the steps of (a) forming the quotient from the change of the measured value of the physiological parameter $\Delta S_{02}$ within relatively short time ranges $\Delta t_{1(4)}$ divided by the maximum change of the measured value $\Delta S_{02max}$ within relatively long time ranges $\Delta t_0$ in order to determine the control value $B_{S1(4)}$, thus $$B_{S1(4)} = \frac{\Delta S_o \cdot \Delta t_o}{\Delta S_{02max} \cdot \Delta t_{1(4)}}$$

(b) regulating the stimulation frequency (f) of the heart pacemaker, with a utilization of the central venous oxygen saturation as physiological parameter depending on the control value $B_{S1(4)}$, in such a manner that always the greatest possible blood oxygen saturation is achieved with the lowest possible stimulation frequency, and (c) measuring the central venous oxygen saturation by means of an optical measuring probe (M) in such a manner that the light emitted by a light-emitting element (32) and reflected by the blood (44) causes an electrical current flow in a light-receiving element (37) which effects, at a constant voltage ($U_K$) of the measuring probe, an increase ($\Delta I_S$) of the flow of current ($I_S$) through the measuring probe, or at a constant flow of current $I_K$, a damping ($\Delta U_S$) of the probe voltage ($U_S$).

2. A process as claimed in claim 1, wherein a follow-up control (17) regulates the stimulation frequency (f) of the heart pacemaker in such a manner that, for changes in the oxygen saturation $\Delta S_{O2}$ per time unit $\Delta t_1$, the stimulation frequency (f) is changed by the amount $\Delta f_1$ after a further time interval $\Delta t_2$, thus a $$(+) \frac{\Delta f_1}{\Delta t_2}$$

results in each case, as long as the absolute value of the measured change in the oxygen saturation is greater than $A_1$ wherein:

$$|B_{S1}| > A_1$$

and wherein:

$$-\frac{\Delta f_1}{\Delta t_2} \text{ after } + B_{S1}$$

or $$+\frac{\Delta f_1}{\Delta t_2} \text{ after } - B_{S1}$$

are only effected until a prescribed limiting value $f_{min}$ or $f_{max}$ is reached.

3. A process as claimed in claim 1, wherein a second, optimizing regulation regulates the stimulation frequency (f) in such a manner that it independently causes a change, with time, in the stimulation frequency $$(-)^{+} \frac{\Delta f_2}{\Delta t_3},$$

at time intervals $\Delta t_5$ in which the amount of the measured quantity $B_{S1}$ is smaller than the value $A_1$, thus $$|B_{S1}| < A_1,$$

and, after a further time interval $\Delta t_4$, evaluates the measured quantity ($\pm$) $B_{S4}$ to the effect that a positive frequency change is only retained if it has caused a positive change in the oxygen saturation, if, therefore:

$$+B_{S4} > A_2 \text{ after } +(\Delta f_2/\Delta t_3)$$

and a negative frequency change is always retained if it does not cause a negative change in the blood oxygen saturation, if, therefore:

$$B_{S4} > -A_2 \text{ after } -(\Delta f_2/\Delta t_3).$$

4. A process as claimed in claim 1, wherein the optimizing regulation of the stimulation frequency has a tendency to a fixed frequency $f_0$ which is achieved by the independent frequency change ($\Delta f_2/\Delta t_3$) more frequently being negative if the stimulation frequency is greater than a prescribed fixed value $f_0$, and by ($\Delta f_2/\Delta t_3$) more frequently being positive if the stimulation frequency is smaller than $f_0$.

5. A process as claimed in claim 3, wherein, in the case in which $|B_{S1}|>A_1$, a check is provided which determines whether an independent frequency change $\Delta f_2$ has previously taken place in the period $\Delta t_5$ and which sign the frequency change had, and which reverses this change if it is opposed to the answer, provided by the follow-up control, to $|B_{S1}|>A_1$, a check, therefore, which ensures the dominance of the follow-up control over the optimum regulation.

6. A process as claimed in claim 1, wherein a program control starts the data acquisition and evaluation directly before or after the emission of the stimulation pulse, or after receiving the detection signal in the case of a self-excitation of the heart.

7. A process as claimed in claim 1, wherein the value of the measured pulse of the constant voltage ($U_K$) or the constant current ($I_K$) for a long time depends on the value $S_{O2max}$ stored in the maximum value storage (14) in such a manner that a value for $S_{O2max}$ sufficient for the required measuring accuracy is achieved with a minimum current consumption of the measuring probe.

8. A process as claimed in claim 1, wherein a check is provided, which detects, by a comparison with limiting values, an error during the data acquisition, the data evaluation and the frequency regulation, and, in each case of error, switches the stimulation frequency to a fixed value, and galvanically switches two electric supply lines (30, 36) to the measuring probe for the stimulation.

9. A device for the frequency regulation of heart pacemakers having a stimulation frequency which adapts itself to the load conditions of a patient, the central venous blood oxygen saturation being opto-electronically measured as a reference or control quantity for the adaptation, this measurement being carried out with the aid of an intracardiac measuring probe, and the acquisition and evaluation of the measured value occurring by means of a circuit additionally arranged in the heart pacemaker, said device comprising (a) an optical measuring probe (M) containing at least one combination of only two active optoelectronic elements, namely a light-emitting element (32) and a light-receiving element (37), as well as additionally at least one semiconductor element ($D_o$);

(b) a control circuit (7) electrically connected to the measuring probe (M), said control circuit generating with the aid of the measuring probe (M) a measuring signal ($U_M$);

(C) a stimulation catheter (K) in which the measuring probe (M) is incorporated;

(d) at least two electric lines (30, 36; $30^1$, $36^1$) leading through the stimulation catheter and electrically connecting the optical measuring probe (M) to the control circuit (7), and (e) a signal evaluating and converting circuit (8) including means to separate the measured signals ($U_M$) attained with the optical measuring probe (M) and the control circuit (7) from interfering signals, amplify said measured signals and convert said measured signals into a signal form suitable for a digital frequency regulation;

(f) said measuring probe (M) comprising a body of two mutually insulated metallic annular elements (31, 34; $31^1$, $34^1$), each of which serves as a carrier of at least one light-emitting element (32) or light-receiving element (37) and which, at the same time, are electrical connectors to the electric lines (30, 36; $30^1$, $36^1$) serving as probe supply lines.

10. A device as claimed in claim 9, wherein the light-emitting element (32) is a light-emitting diode and the light-receiving element (37) is a phototransistor, said diode (32) and said phototransistor (37) being connected with one another in parallel, in the measuring probe (M), in such a manner that, when an npn or pnp phototransistor is used, the cathode of the diode (32) is connected with one of the emitter and collector of the phototransistor (37) and the anode of the diode (32) is connected with the other of the emitter and collector of the phototransistor (37).

11. A device as claimed in claim 9, wherein several light-emitting elements (32) and light-receiving elements (37) are arranged on the metallic annular elements, circularly around the axis of the catheter, in such a manner that the measuring angle in the cross-sectional plane of the catheter can be up to 360°.

12. A device as claimed in claim 9, wherein both electric supply lines (30, $30^1$; 36, $36^1$) to the measuring probe (M) are used as supply lines to the stimulation electrode (E).

13. A device as claimed in claim 10, wherein a semiconductor diode $D_o$ is integrated into the measuring probe (M) in such a manner that the cathode of the diode $D_o$ is connected with the anode of the ligth-emitting diode (32) and the anode of the diode $D_o$ is connected with the cathode of the light-emitting diode (32).

14. A device as claimed in claim 9, wherein a transparent protective jacket (39) is mounted around the body of the measuring probe (M) to prevent the penetration of blood constituents.

15. A device as claimed in claim 9, wherein the electric line (30, $30^1$) is constructed as a wire winding and the measuring probe (M) is arranged between said wire winding and an other transparent insulation tube (41) in such a manner that the latter is neither interrupted nor substantially deformed.

16. A device as claimed in claim 12, wherein the measuring probe (M) is integrated into the stimulation catheter (K) in such a manner that the measuring probe can be positioned in the region of the atrioventricular valves during implantation about 4 to 8 cm behind the stimulation electrode (E).

17. A device as claimed in claim 9, wherein the control circuit (7) of the measuring probe (M) is an electrical pulse generator arranged to produce a positive and a negative pulse of controlled voltage ($U_K$) or current ($I_K$) which are then passed on, via at least one load resistance ($R_v$) to the probe supply lines (30, $30^1$; 36, $36^1$) and to the measuring probe (M) in such a manner that the voltage ($U_M$) at the load resistance ($R_v$) can be used as a measured value.

18. A device as claimed in claim 9, wherein the signal converter circuit (8) includes means for evaluating the positive and negative pulses ($+U_{MM}$, $-U_{MF}$) sequentially applied at the load resistance ($R_v$) in such a manner that the measuring errors included in the proper measured pulse ($U_{MM}$) caused by changes in the resistances of the electric lines (30, $30^1$; 36, $36^1$) and a temperature drift of the measuring probe (M) are eliminated.

* * * * *